United States Patent [19]

Takata et al.

[11] 4,452,682

[45] Jun. 5, 1984

[54] APPARATUS FOR MEASURING CLINICAL EMERGENCY CHECK ITEMS OF BLOOD

[75] Inventors: Yoshinori Takata, Ibaraki; Hiroyuki Miyagi, Mito; Kunio Hirota, Hitachi; Yasuhisa Shibata; Kazuo Nidaira, both of Ibaraki; Fusao Shirato, Hitachi, all of Japan

[73] Assignee: Hitachi, Ltd., Tokyo, Japan

[21] Appl. No.: 200,264

[22] Filed: Oct. 24, 1980

[51] Int. Cl.³ .............................................. G01N 27/46
[52] U.S. Cl. .................................. 204/403; 204/416; 204/400; 204/415
[58] Field of Search ........... 204/195 B, 195 P, 195 M, 204/1 T, 195 R, 195 G; 23/253 R, 230 B; 128/2 E, 2 G

[56] References Cited

U.S. PATENT DOCUMENTS 3,556,950 1/1971 Dahms .......................... 204/195 R
3,963,440 6/1976 Stein et al. ................. 204/195 P X

FOREIGN PATENT DOCUMENTS 48-51695 7/1973 Japan ............................ 204/195 R

OTHER PUBLICATIONS

Schindler et al., *Chimia* 31 (1977), No. 10, pp. 404–407.
*Clinical Chemistry*, vol. 23, No. 9, pp. 1718–1725, (1977).

*Primary Examiner*—Ta-Hsung Tung
*Attorney, Agent, or Firm*—Antonelli, Terry & Wands

[57] ABSTRACT

An apparatus for electrochemically measuring clinical emergency check items of blood for a short time by flowthrough system, using a small amount of whole blood as a blood sample, which comprises a blood pH/gas component sensor unit, an electrolyte component sensor unit, and/or a biochemical component sensor unit, arranged in series in this order, a sampler and these sensor units being communicated with one another through a blood sample flow passage or channel, each of the sensor units being provided with sensor electrodes and at least one reference electrode as electrochemical sensor means.

Detected values from each of the sensor units are transmitted to a computer or calculator through a current amplifier and/or a differential amplifier for a differential voltage from the voltage of the reference electrode to compute pH, pressure, or concentrations from the detected values, and numerically displayed on a display device connected to the computer.

12 Claims, 8 Drawing Figures

APPARATUS FOR MEASURING CLINICAL EMERGENCY CHECK ITEMS OF BLOOD

BACKGROUND OF THE INVENTION

This invention relates to an apparatus for measuring clinical emergency check items of blood, and more particularly to an apparatus for electrochemically measuring pH, gas component pressure or concentration, electrolyte component (for example, sodium ion, potassium ion, calcium ion, etc.) concentrations, biochemical component (for example, glucose, urea-form nitrogen, etc.) concentrations of blood by flowthrough system within a very short time, using a small amount of whole blood as a blood sample.

Recently, apparatuses for automatic analysis of blood coponents have been widely used, and are indispensable for diagnosis of disease because of precise and rapid diagnosis. Particularly, use of electrodes as sensors has been proposed. For example, measurement of pH, carbon dioxide pressure and oxygen pressure or concentration in blood by means of a pH electrode, a $P_{CO_2}$ electrode and a $P_{O_2}$ electrode was proprosed [Clinical Chemistry 23 (a) 1718 (1977), Japanese Laid-open Patent Application No. 51695/73]. Continuous direct measurement of electrolyte component (sodium ion, potassium ion and calcium ion) concentrations and β-D-glucose concentration of blood by means of ion-selective electrodes was proposed [Chimia 31 (1977), No. 10 (October)]. Furthermore, continuous measurement of oxygen, carbon dioxide and electrolyte components of blood was proposed (U.S. Pat. No. 3,556,950).

SUMMARY OF THE INVENTION

An object of the present invention is to provide an apparatus for electrochemically measuring clinical emergency check items of blood by flowthrough system with a high precision in a short time, using a small amount of whole blood as a blood sample.

According to the present invention, an apparatus for electrochemically measuring emergency check items of blood comprises a pH/gas component sensor unit, an electrolyte component sensor unit, and/or a biochemical component sensor unit, arranged in series in this order, and a sampler is communicated with these sensor units through a blood sample flow passage or channel. Sensor electrodes and at least one reference electrode are provided as an electrochemical sensor means in each of the sensor units and a sample inlet is provided between the sensor units to make each sensor unit function as an independent unit according to the necessity, that is, according to the type of disease.

Detected value of each sensor unit is transmitted to a computer or a calculator through a current amplifier and/or a differential amplifier for a difference voltage from the voltage of the reference electrode to compute pH, pressure or concentration from the detected value, and numerically displayed on a display device connected to the computer.

According to the present invention, electrochemical sensor means (electrodes) are used as sensors for detecting the individual check items, as described above, to obtain detected values (signal output) as direct current values or differential voltages from the voltage of the reference electrode, and also gas-permeating membranes, ion-selective membranes, and immobilized enzyme are provided on the electrodes to assure the selectivity. Thus, the amount of sample blood can be considerably reduced, and analysis can be carried out by flowthrough system without any addition of an analytical reagent in the course of analysis.

In the present invention, it is important to provide the pH/gas component sensor unit at the most upstream side, because measurement of pH and gas components of blood is preferential to other emergency check items, and an influence of measurement error due to the permeated solution from electrolyte component sensor electrodes or reference electrodes, which occurs when the pH/gas component sensor unit is arranged at the downstream side of the electrolyte component sensor unit, can be eliminated.

According to the present invention, at least one reference electrode is provided in each of the sensor units, and each sensor unit can be independently used for measurement according to the necessity, that is, according to the type of disease, as described above, and furthermore, measurement precision of each component can be increased when all the sensor units are used in series for measurement.

According to the present invention, a dialysis cell can be provided between the sensor units according to the necessity, and more rapid analysis of whole blood can be carried out by dialysis only of desired components.

The present invention will be described in detail below according to embodiments of the present invention, referring to the accompanying drawings.

PREFERRED EMBODIMENTS OF THE INVENTION

Figure 1:
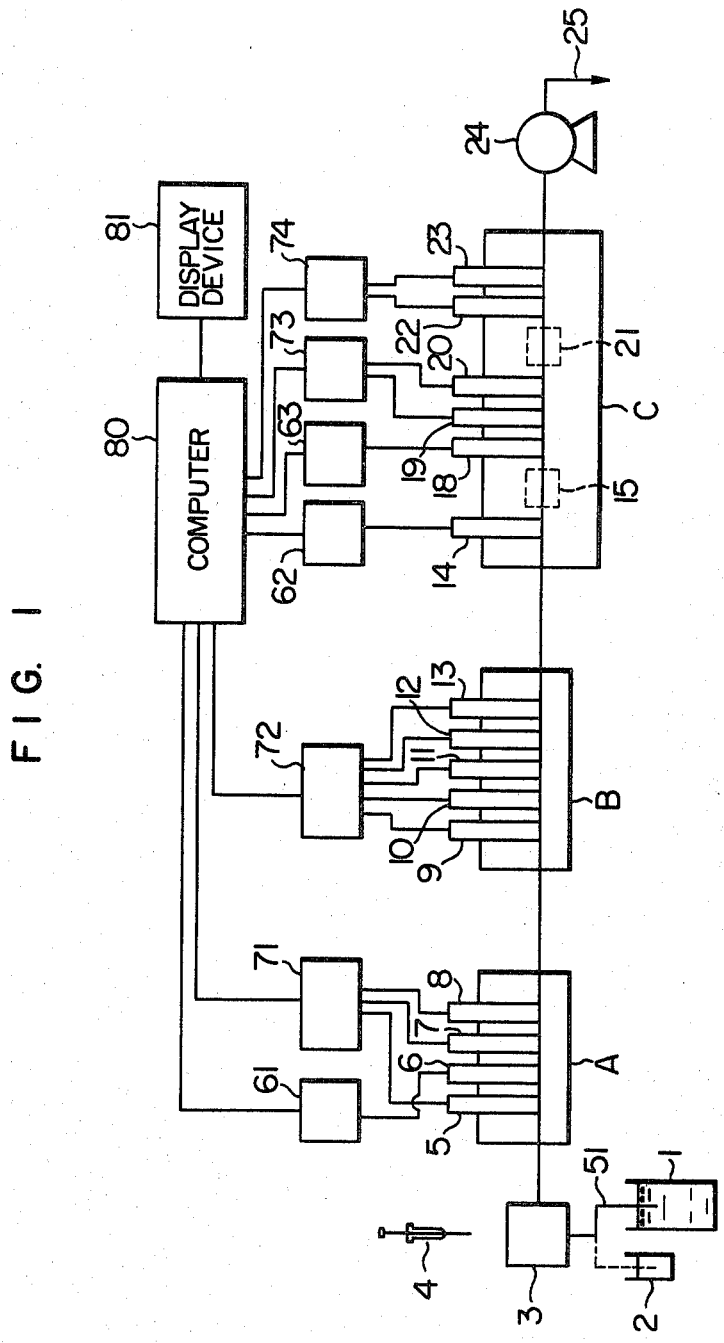
FIG. 1 is a schematic flow diagram showing one embodiment of the present invention.

One embodiment of the present invention is shown in FIG. 1.

0.2–0.5 ml of a standard solution is introduced from a standard solution tank 1 into a flow passage or channel by a sampler 3 through a moving nozzle 51 through suction by a pump 24. The standard solution also acts as a washing solution for the flow passage or channel. A definite amount, for example, 100–250 ml, of sample blood is taken from a sample cup 2 through the moving nozzle 51, which moves between the standard solution tank 1 and the sample cup 2, into the sampler 3 or injected therein by a microsyringe 4. The bood sample thus introduced into the flow passage or channel moves through the flow passage or channel as a band inserted between two portions of the standard solution. The sample enters a blood pH/gas component sensor unit A at first, and passes under and in contact with a pH sensor electrode 5, a $P_{O_2}$ (oxygen partial pressure) sensor electrode or dissolved oxygen sensor electrode 6, a $P_{CO_2}$ (carbon dioxide partial pressure sensor electrode or $HCO_3^-$ (bicarbonate ion) selective sensor electrode 7, and a reference electrode 8.

The lead wires of electrodes 5, 7, and 8 are connected to a differential amplifier 71 and a voltage difference between the individual sensor electrodes and the reference electrode 8 is measured, whereas the lead wire of electrode 6 is connected to a current amplifier 61 to measure a reduction current of dissolved oxygen. The amplified signals from differential amplifier 71 and current amplifier 61 are transmitted, as signals specific to the individual sensor electrodes, to a computer or calculator 80, for example, a microcomputer, and these individual signals are computed as pH, component concentrations or gas pressures, and displayed as pH, concentrations or gas pressures on a display device 81. The displayed data can be printed out. In the computation of desired components, calibration of computer 80 should be made with the standard samples in advance.

Then, the sample having passed through the blood pH/gas coponent sensor unit A is led to an electrolyte component sensor unit B, where the sample passes under and in contact with a Na+ (sodium ion) sensor electrode 9, a K+ (potassium ion) sensor electrode 10, an NH4+ (ammonium ion sensor electrode and/or Ca+ (calcium ion) sensor electrode 11, a Cl− (chloride ion) electrode 12, and a reference electrode 13, and voltage differences between the individual sensor electrodes and the reference electrode are measured in a differential amplifier 72, computed in the computer 80 and displayed on the display means 81 in the same manner as above.

Then, the sample enters a biochemical component sensor unit C, where a dissolved oxygen concentration is detected by a $P_{O_2}$ (oxygen partial pressure) sensor electrode 14, and measured in a current amplifier 62, and the resulting signal is transmitted to the computer 80. Then, the sample passes through an enzyme reactor 15 containing immobilized glucose oxidase (GOD). The glucose in the sample consumes the dissolved oxygen to produce gluconic acid and hydrogen peroxide. The amount of consumed oxygen is detected by a $P_{O_2}$ sensor electrode 18, and measured in a current amplifier 63, and the resulting signal is transmitted to the computer 80, and a glucose concentration is computed from the difference from the signal from the sensor electrode 14, and displayed on the display device 81. It is possible to replace the $P_{O_2}$ sensor electrodes 14 and 18 with a $H_2O_2$ (hydrogen peroxide) sensor electrode (in this case $H_2O_2$ electrode 14 can be eliminated) and measure the amount of formed $H_2O_2$ to determine the glucose concentration.

After the measurement of the glucose concentration, the sample is passed through a urease-immobilized enzyme reactor 21 to detect the amounts of $NH_4^+$ (ammonium ions) at the upstream side and the downstream side of the reactor by means of $NH_4^+$ sensor electrodes 19 and 22 and reference electrodes 20 and 23, and a urea-form nitrogen concentration of the sample is measured in differential amplifiers 73 and 74 from the differential values and displayed on the display device 81 through the computer 80. Then, the sample is discharged through the pump 24 and a discharge line 25. The sensor units A and B each are comprised of one block, but the sensor unit C is practically comprised of electrode blocks and enzyme-immobilized columns separately. The entire sensor unit C can be, of course, comprised of one block.

Figure 5A:
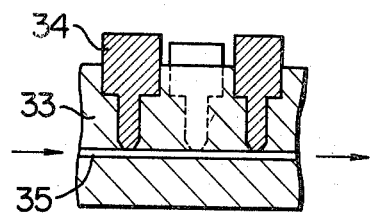
FIGS. 5 (a), (b) and (c) are views showing an electrode arrangement in a sensor unit.
Figure 5B:
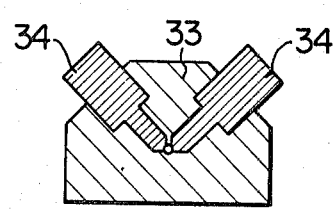
Figure 5C:
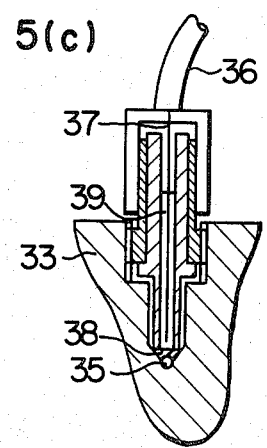

A plurality of electrodes are arranged in series in one block, as shown in FIG. 5, but can be divided into smaller blocks, if necessary, or the entire electrodes can be arranged in one block, without impairing the object and effect of the present invention. Resident time through these three sensor units is about 3 minutes.

Figure 2:
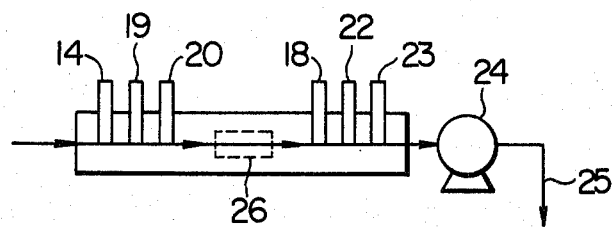
FIG. 2 is a schematic flow diagram showing another embodiment of the present invention.

In FIG. 2, another embodiment of the present invention is shown, where an enzyme reactor with two kinds of immobilized glucose oxidase and urease is used. A $P_{O_2}$ sensor electrode 14, a $NH_4^+$ sensor electrode 19 and a reference electrode 20 are provided at the upstream side of the reactor, and a $P_{O_2}$ sensor electrode 18, a $NH_4^+$ sensor electrode 22, and a reference electrode 23 are provided at the downstream side of the reactor, whereby the volume of the entire sensor unit is reduced, a shorter response time is obtained, and particularly the concentration diffusion in the enzyme reactor and at the line joints can be effectively reduced. As the enzyme reactor, uricase, creatininase, etc. can be supplemented or substituted for the glucose oxidase and urease, if necessary, to determine uric acid and creatinine concentrations.

Figure 3:
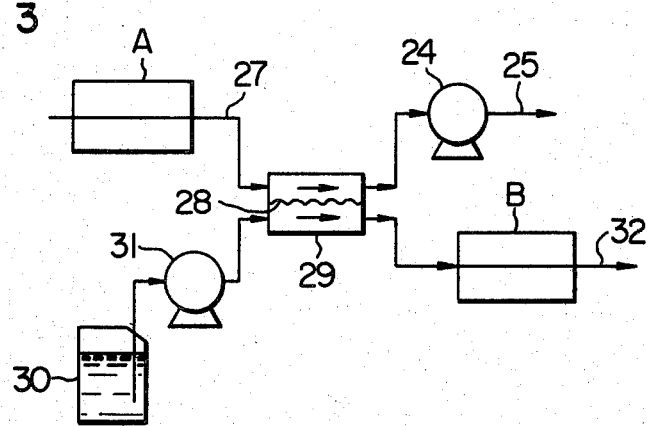
FIG. 3 is a schematic flow diagram showing further embodiment of the present invention.

In FIG. 3, a further embodiment of the present invention is shown, where a dialysis cell 29 is provided between the pH/gas component sensor unit A and the electrolyte component sensor unit B. After the measurement of pH, gas component concentration or gas pressure, the sample enters a dialysis cell 29 through a line 27 and discharged through a pump 24. On the other hand, a buffer solution is introduced into an opposite cell compartment partitioned by a dialysis membrane 28 in the dialysis cell from a buffer solution tank 30, and the electrolyte components and biochemical components (substrates) to be detected by application of enzyme is extracted from the sample into the buffer solution thereby. By use of the dialysis cell, fouling of the electrodes due to the fouling components of blood can be prevented, and also a buffer solution suitable for the reaction in an immobilized enzyme reactor can be selected, though there is such a disadvantage as a little delay in speed of response. Flow passage 32 leads the buffer solution to the $P_{O_2}$ electrode 14. The dialysis cell 29 can be also provided at the downstream side of electrolyte component sensor unit B to reduce the delay in speed of response up to the measurement of electrolyte components. Furthermore, the enzyme reactor can be replaced with an enzyme electrode, that is, a $P_{O_2}$ or $H_2O_2$ sensor electrode 18 or a $NH_4^+$ sensor electrode 22 with an immobilized enzyme membrane covering the sensor membrane side to make a structure of the sensor unit hardly fouled and measure the emergency check items of whole blood without using any dialysis cell.

Figure 4:
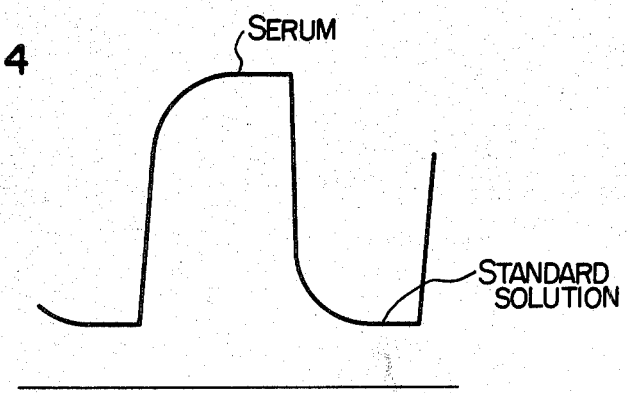
FIG. 4 is a diagram showing an example of electrode response according to the present invention.

In FIG. 4, a response curve of a sensor electrode selected from the apparatus of FIG. 1 is shown. That is, an output of K+ sensor electrode is recorded as a voltage difference when a standard solution of 4.0 mEq K+/l and serum are passed alternately at intervals of 30 seconds, and a K+ concentration of 4.4 mEq/l computed against 4.0 mEq K+/l is displayed on the display device. Similar response curves can be obtained for other sensor electrodes, and concentrations of the individual components are shown on the display device.

In FIGS. 5 (a), (b) and (c) are shown an example of sensor electrode arrangement in the flow passage, where FIG. 5 (a) is a side view of an electrode block, FIG. 5 (b) a front view of the electrode block, and FIG. 5 (c) an enlarged view of an electrode. An electrode block (flow cell) 33 has a flow passage or channel 35 and a plurality of sensor electrodes 34 are so arranged that sensor membranes 38 of the individual sensor electrodes can be in the flow passage 35. Sensor electrodes 34 contain an internal solution (electrolyte solution) 39, and an Ag/AgCl electrode wire immersed in the internal solution is connected to an amplifier through a lead wire 36.

Figure 6:
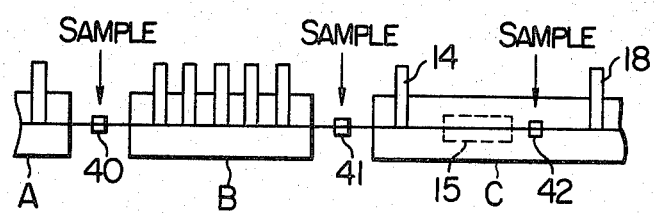
FIG. 6 is a schematic flow diagram showing a still further embodiment of the present invention.

In FIG. 6, a still further embodiment of the present invention is shown, where sample inlets 40, 41 and 42 are provided between the sensor units A, B and C, or blocks in the sensor unit C, and a sample can be introduced into any of the sample inlets by a microsyringe or a sampler to selectively measure only the electrolyte and/or biochemical components in a shorter time. Such selective by-passing is effective when all the check items are not necessary to measure.

What is claimed is:

1. An apparatus for measuring blood emergency check items by electrochemically measuring pH, gas component concentrations or pressures, and electrolyte component concentrations of whole blood by a flow-through system, which comprises:
   (1) a sampler,
   (2) a blood pH/gas component sensor unit comprising a flow cell provided with a pH sensor electrode, at least one gas sensing electrode and a reference electrode.
   (3) a blood electrolyte component sensor unit comprising a flow cell provided with a plurality of ion sensing electrodes and a reference electrode, the sampler and the sensor units being arranged separately from each other and in series in the order given, and
   (4) a blood sample flow passage providing successive communication between the sampler, the blood pH/gas component sensor unit, and the blood electrolyte component sensor unit.

2. An apparatus for measuring blood emergency check items by electrochemically measuring pH, gas component concentrations or pressures, and biochemical component concentrations of whole blood by a flowthrough system, which comprises:
   (1) a sampler,
   (2) a blood pH/gas component sensor unit comprising a flow cell provided with a pH sensor electrode, at least one gas sensing electrode and a reference electrode.
   (3) a blood biochemical component sensor unit comprising a flow cell provided with immobilized enzyme and a reference electrode, the sampler and the sensor units being arranged separately from each other and in series in the order given, and
   (4) a blood sample flow passage providing successive communication between the sampler, the blood pH/gas component sensor unit, and the blood biochemical component sensor unit.

3. An apparatus for measuring blood emergency check items by electrochemically measuring pH, gas component concentrations or pressures, electrolyte component concentrations, and biochemical component concentrations of whole blood by a flowthrough system, which comprises:
   (1) a sampler,
   (2) a blood pH/gas component sensor unit comprising a flow cell provided with a pH sensor electrode, at least one gas sensing electrode and a reference electrode,
   (3) a blood electrolyte component sensor unit comprising a flow cell provided with a plurality of ion sensing electrodes and a reference electrode,
   (4) a blood biochemical component sensor unit comprising a flow cell provided with immobilized enzyme and a reference electrode, the sampler and the sensor units being arranged separately from each other and in series in the order given.
   (5) a blood sample flow passage providing successive communication between the sampler, the blood pH/gas component sensor unit, the blood electrolyte component sensor unit, and the blood biochemical component sensor unit.

4. An apparatus according to claim 1, 2 or 3, wherein the blood pH/gas component sensor unit comprises a pH sensor electrode, a $P_{O_2}$ sensor electrode, or dissolved oxygen sensor electrode, a $P_{CO_2}$ sensor electrode or a bicarbonate selective sensor electrode, and a reference electrode, the sensing side of each of the electrodes is in the blood sample flow passage, while the connecting side thereof is connected to a computer through a current amplifier or a differential amplifier for a differential voltage from voltage of the reference electrode, and the computer is connected to a display device, each of resulting signals being numerically displayed on the display device as pH, oxygen concentration or pressure, bicarbonate concentration upon computation in the computer.

5. An apparatus according to claim 1 or 3, wherein the blood electrolyte component sensor unit comprises a sodium ion sensor electrode, a potassium ion sensor electrode, an ammonium ion sensor electrode and/or a calcium ion sensor electrode, a chloride ion sensor electrode, and a reference electrode, the sensing side of each of the electrodes is in the blood sample flow passage, while the connecting side thereof is connected to a computer through a differential amplifier for a differential voltage from voltage of the reference electrode, the computer is connected to a display device, each of signals being numerically displayed on the display device as a sodium ion concentration, a potassium ion concentration, an ammonium ion concentration, and/or a calcium ion concentration, or a chloride ion concentration upon computation in the computer.

6. An apparatus according to claim 2 or 3, wherein the blood biochemical component sensor unit with immobilized enzyme comprises electrodes with immobilized enzyme reactor and reference electrodes, the sensing side of each of the electrodes is in a blood sample flow passage, while the connecting side thereof is connected to a computer through a current amplifier or a differential amplifier for a differential voltage from the voltage of the reference electrode, the computer is connected to a display device, each of signals being numerically displayed as a biochemical component concentration upon computation in the computer.

7. An apparatus according to claim 1, 2 or 3, where a dialysis cell is provided between the sensor units.

8. An apparatus according to claim 1, 2 or 3, wherein sample inlets are provided between the sensor units.

9. An apparatus for measuring blood emergency check items by electrochemically measuring pH, gas component concentrations or pressures, electrolyte component concentrations, and biochemical component concentrations of whole blood by a flowthrough system, which comprises:
   (1) a blood pH/gas component sensor unit comprising a flow cell provided with a pH sensor electrode, a $P_{O_2}$ sensor electrode and a reference electrode, the $P_{O_2}$ sensor electrode being connected to a current amplifier, and the pH sensor electrode and the reference electrode being connected to a differential amplifier, (2) a blood electrolyte component sensor unit comprising a flow cell provided with a plurality of ion sensing electrodes and a reference electrode, the plurality of the ion sensing electrodes being directed to detecting voltage potential, (3) a blood biochemical component sensor unit provided with a glucose sensor means and a urea-form nitrogen sensor means, the glucose sensor means having a reactor containing immobilized glucose oxidase and either a pair of $P_{O_2}$ sensor electrodes provided before and after the reactor containing immobilized glucose oxidase or a $P_{H_2O_2}$ sensor electrode provided after the reactor containing immobilized glucose oxidase, the urea-form nitrogen sensor means being provided with a reactor containing immobilized urease, a pair of ammonium ion sensor electrodes provided before and after the reactor containing immobilized urease, and a pair of reference electrodes, and (4) the sensor units being arranged separately from each other and in series in the order given.

10. The apparatus according to claim 9, wherein a sample inlet is provided at the upstream side of each of the sensor units.

11. The apparatus according to claim 9, wherein the reactor containing immobilized glucose oxidase is a first reactor and the reactor containing immobilized urease is a second reactor separate from said first reactor.

12. The apparatus according to claim 9, wherein the reactor containing immobilized glucose oxidase and the reactor containing immobilized urease constitute a single reactor.

* * * * *